US007785769B2

(12) United States Patent
Spector et al.

(10) Patent No.: US 7,785,769 B2
(45) Date of Patent: *Aug. 31, 2010

(54) IMMOBILIZATION OF OLIGONUCLEOTIDES AND PROTEINS IN SUGAR-CONTAINING HYDROGELS

(75) Inventors: Mark S. Spector, Springfield, VA (US); David A. Stenger, Herndon, VA (US); Charles H. Patterson, Jr., Glen Burnie, MD (US); Brett D. Martin, Washington, DC (US); Paul T. Charles, Bowie, MD (US)

(73) Assignee: The United States of America as reprsented by the Secretary of the Navy, Washington, DC (US)

( * ) Notice: Subject to any disclaimer, the term of this patent is extended or adjusted under 35 U.S.C. 154(b) by 603 days.

This patent is subject to a terminal disclaimer.

(21) Appl. No.: 10/627,143

(22) Filed: Jul. 25, 2003

(65) Prior Publication Data
US 2005/0019884 A1    Jan. 27, 2005

(51) Int. Cl.
*C12Q 1/00*    (2006.01)
(52) U.S. Cl. .............................. 435/4; 435/6; 435/287.2; 435/14; 526/72; 526/89; 530/300; 530/350
(58) Field of Classification Search .................... 435/4, 435/6, 7.1, 34, 14, 8; 526/72, 89; 530/300, 530/350
See application file for complete search history.

(56) References Cited

U.S. PATENT DOCUMENTS

| | | | |
|---|---|---|---|
| 5,854,030 A | 12/1998 | Dordick et al. | |
| 5,932,711 A | 8/1999 | Boles et al. | |
| 5,981,734 A | 11/1999 | Mirzabekov et al. | |
| 6,180,770 B1 | 1/2001 | Boles et al. | |
| 2003/0218130 A1* | 11/2003 | Boschetti et al. | 250/288 |

OTHER PUBLICATIONS

Chen et al. Macromolecules (1995) 28: 6014-6019.*
Timofeev et al, "Regioselective Immobilization of Short Oligonucleotides to acrylic copolymer Gels", Oxford University Press 1996 pp. 3142-3149.
Pease et al, "Light-Generated Oligonucleotide Arrays for Rapid DNA Sequence Analysis", Proc. National Academy of Science, May 1994, vol. 91, pp. 5022-5026.
Chrisey et al, "Covalent Attachment of Synthetic DNA to Self-Assembled Monlayer Films",Oxford University Press 1995 pp. 3031-3039.
Zammatteo et al, "Comparison between Different Strategies of Covalent Attachment of DNA to Glass Surfaces to Build DNA Mircroarrays", Academic Press, Nov. 11, 1999, Analytical Biochemistry 280, pp. 143-150.
Guschin at al, "Manual Manufacturing of Oligonucleotide, DNA, and Protein Microchips", Academic Press, Analytical Biochemistry 250, pp. 203-211.
Martin et al, "Macromolecules", American Chemical Society, Dec. 21, 1992, vol. 25, No. 26, pp. 7081-7085.
Martin et al, "Highly Swellings Hydrogels From Ordered Galactose-Based Polyacrylates", Elsevier Science Ltd., 1998, Biomaterials 19, pp. 69-76.
Schena et al, "Quantitative Monitoring of Gene Expression Patterns with a Complementary DNA Microarray", JSTOR: Science, Oct. 20, 1995, vol. 270, pp. 467-469.
Bordignon et al, "Gene Therapy in Peripheral Blood Lymphocytes and Bone Marrow for ADA Immunodeficient Patients", JSTOR: Science, Oct. 20,1995, vol. 270, pp. 470.

* cited by examiner

*Primary Examiner*—Irene Marx
*Assistant Examiner*—Susan Hanley
(74) *Attorney, Agent, or Firm*—Amy Resing; Stephen T. Hunnius

(57) ABSTRACT

The use of sugar-containing hydrogels as very highly porous, aqueous support material for the immobilization of oligonucleotides, peptides, proteins, antigens, antibodies, polysaccharides, and other biomolecules for sensor applications. Unusually large sizes of interconnected pores allow large target molecules to pass rapidly into and through the gel and bind to immobilized biomolecules. Sugar-containing hydrogels have extremely low non-specific absorption of labeled target molecules, providing low background levels. Some hydrogel materials do not have this type of homogeneous interconnected macroporosity, thus large target molecules cannot readily diffuse through them. Additionally, they nearly always experience non-specific absorption of labeled target molecules, limiting their usefulness in sensor applications. A method is provided for preparing sugar polyacrylate hydrogels with functional chemical groups which covalently bond oligonucleotides and peptides. A method for copolymerizing acrylate-terminated oligonucleotides with sugar acrylate monomers and diacrylate cross-linking agents is also provided.

8 Claims, 9 Drawing Sheets

BS³

EDC

IMMOBILIZATION OF OLIGONUCLEOTIDES AND PROTEINS IN SUGAR-CONTAINING HYDROGELS

BACKGROUND OF THE INVENTION

Field and Background of the Invention

Immobilization of deoxyribonucleic acid (DNA), ribonucleic acid (RNA), proteins, antigens, and other biomolecules on a variety of solid substrates, typically glass, provides the basis for array-based bioassays. Examples of such technologies include patterning of DNA probes in hybridization assays for clinical diagnostics, drug discovery, and pathogen detection and arraying proteins and antigens for antibody detection. A number of strategies have been developed for the attachment of oligomers to glass substrates. Single-stranded DNA (ssDNA) probes are commonly synthesized on surfaces photolithographically, Pease et al, *Proc. Natl. Acad. Sci. U.S.A.* 1994, 91, 5022-5026, electrostatically adsorbed to the substrate, Schena et al, *Science* 1995, 270, 467-470 or covalently attached to a self-assembled monolayer, Chrisey et al, *Nucleic Acid Res.* 1996, 24, 3031-3039, Zammatteo et al, *Anal Biochem.* 2000, 280, 143-150, A major limitation for the use of microarrays in pathogen detection is the low signal levels observed when probe DNA is confined to the substrate surface. An alternative is immobilizing ssDNA in a three-dimensional hydrogel allowing for higher density and sensitivity, Timofeev et al, *Nucleic Acid Res.* 1996, 24, 3142-3149. U.S. Pat. No. 5,981,734 describes a method for immobilizing biomolecules such as oligonucleotides in polyacrylamide gels, either through copolymerization of allyl-substituted oligonucleotides or incorporation of functional groups which can be covalently coupled to modified oligonucleotides. U.S. Pat. No. 6,180,770 describes a method for preparing oligonucleotides derivatized with a terminal polymerizable acrylamide. These monomers can then be copolymerized into an acrylamide hydrogel to produce a polymerized layer containing the covalently linked ssDNA molecule. This technology has been licensed to Apogent Discoveries and is commercially available.

Conventional hydrogels suffer from a number of limitations. In general, it is difficult to obtain water contents greater than 95 wt %. This results in a small mesh size in the gel, limiting the diffusion of large macromolecules or particles. For example, target ssDNA with length greater than 200 nucleotides are unable to permeate into a standard 5% polyacrylamide gel, Guschin et al, *Anal. Biochem.* 1997, 250, 203-211. The networks are often heterogeneous and the monomers can be toxic (e.g. acrylamide). The polymeric hydrogels described in this Disclosure, for example those based on monomeric sugar acrylates or methacrylates, do not experience the drawbacks outlined above. Enzymatic acryloylation provides a simple method for forming the monomers with high regioselectivity, Martin et al, *Macromolecules*, 1992, 25, 7081-7085. These hydrogels have equilibrium water contents above 95% resulting in pore sizes of 500 nm or larger, Martin et al, *Biomaterials*, 1998, 19, 69-76. U.S. Pat. No. 5,854,030 provides the methodology for the chemoenzymatic synthesis of the monomers and subsequent formation of the hydrogels. The above cited references, including publications and patents are incorporated herein by reference in their entirety.

SUMMARY OF THE INVENTION

This invention details the synthesis of polymeric sugar-containing hydrogels and their use as three-dimensional, highly macroporous substrates for the immobilization of oligonucleotides, peptides, proteins, and other biomolecules. These hydrogels are formed from compounds containing polymerizable double bonds. Examples of such compounds include, but are not limited to, acrylates, methacrylates, acrylamides and methacrylamides. The sugar compounds may be hexose, pentose, tetrose, or triose, or monosaccharide, di-, tri-, tetra-, penta-, hexa-, hepta-, octa-, nona-, or decasaccharides. If glycosides are used, they may contain either alpha or beta aglycon linkages. The hydrogel provides a support with activated functional groups for biomolecule attachment throughout the matrix. The high porosity of the sugar-containing hydrogels allows for rapid diffusion of large (up to two micron diameter) molecules or particles. This includes long DNA sequences (e.g. greater than 100,000 nucleotide bases) and large antibodies, functionalized microbeads as well as semiconductor and metal nanoparticles currently being explored as alternatives to conventional fluorophores for ultrasensitive optical detection. A further advantage of the hydrogel matrix is its extremely low nonspecific absorption of labeled biomolecular targets, and the large number of reactive sites available for molecular attachment. The high density of immobilized probes throughout the volume of the gel leads to a greater detection sensitivity versus a similarly derivatized flat solid substrate.

Three methods for incorporating biomolecules into the sugar-containing hydrogels are disclosed. All methods result in covalent linkage of the biomolecules to the three-dimensional gel matrix. In the first case, oligonucleotides with a terminal acrydine unit are polymerized with a sugar compound having a polymerizable double bond such as a sugar acrylate or sugar methacrylate monomer and a crosslinker having at least two polymerizable double bonds, providing a direct covalent link to the acrylate backbone.

In the second case, a sugar compound having a polymerizable double bond such as a sugar acrylate or sugar methacrylate monomer is polymerized with a crosslinker having at least two polymerizable double bonds and a third compound having a polymerizable double bond and a group selected to allow covalent attachment of oligonucleotides, peptides, proteins, or other biomolecules. The crosslinker and the third compound may contain an acrylate, methacrylate, acrylamide, or methacrylamide moiety. In one instance, amino groups are introduced into the gel by using N-(3-aminopropyl) methacrylamide as a monomer. A number of strategies are then available for the attachment of biomolecule amino groups to the gel polymer. Aldehyde terminated oligonucleotides, peptides, proteins, or other biomolecules react with the amine in the presence of a reducing agent, forming a covalent bond. Phosphorylated or carboxylated oligonucleotides, peptides, proteins, or other biomolecules can be covalently attached to the amino group using carbodiimide condensation mediated by a compound such as EDC. Amino terminated oligonucletide, peptides, proteins, or other biomolecules can be coupled using a homobifunctional crosslinker such as diisothiocyanate or bis(sulfosuccinimidyl) suberate ($BS^3$). In the third instance, carboxyl groups are introduced into the gel by introducing N-(3-carboxylpropyl) methacrylamide as a termonomer. Amino terminated oligonucleotides can be covalently attached to the carboxyl group through carbodiimide condensation. In a final instance, aldehyde groups are introduced into the gel by using N-(5,6-di-O-isopropylidene) hexylacrylamide as a termonomer. Aldehydes can then be generated by removing the isopropylidene protecting groups using acetic acid (Timofeev et al, 1996). Aminated oligonucleotides, peptides, proteins, or other biomolecules can then be reacted with the aldehyde groups, forming covalent linkages. The gels described in this Invention have water contents of at least 90 wt %, and in preferred embodiments have water contents of 94 wt % of greater.

FIGURES

FIG. 1. shows one possible generalized chemical structure of the polymer network component of the sugar-containing hydrogels of this invention. In the preferred embodiments, $R_1$ is H, alkyl or phenyl, $R_2$-$R_7$ are H, OH, O-phenyl, or O-methyl, $R_8$ is H or methyl, $R_9$ is OH, propane 1,3 diamine, or aminohydroxy acetic acid, and $R_{10}$ is H or methyl. $R_9$ can also be a biomolecule covalently attached via an amine linkage. In this Figure the repeat units m, n, and p are residues originating from acrylate, methacrylate, acrylamide, or methacrylamide monomers.

Figure 4:
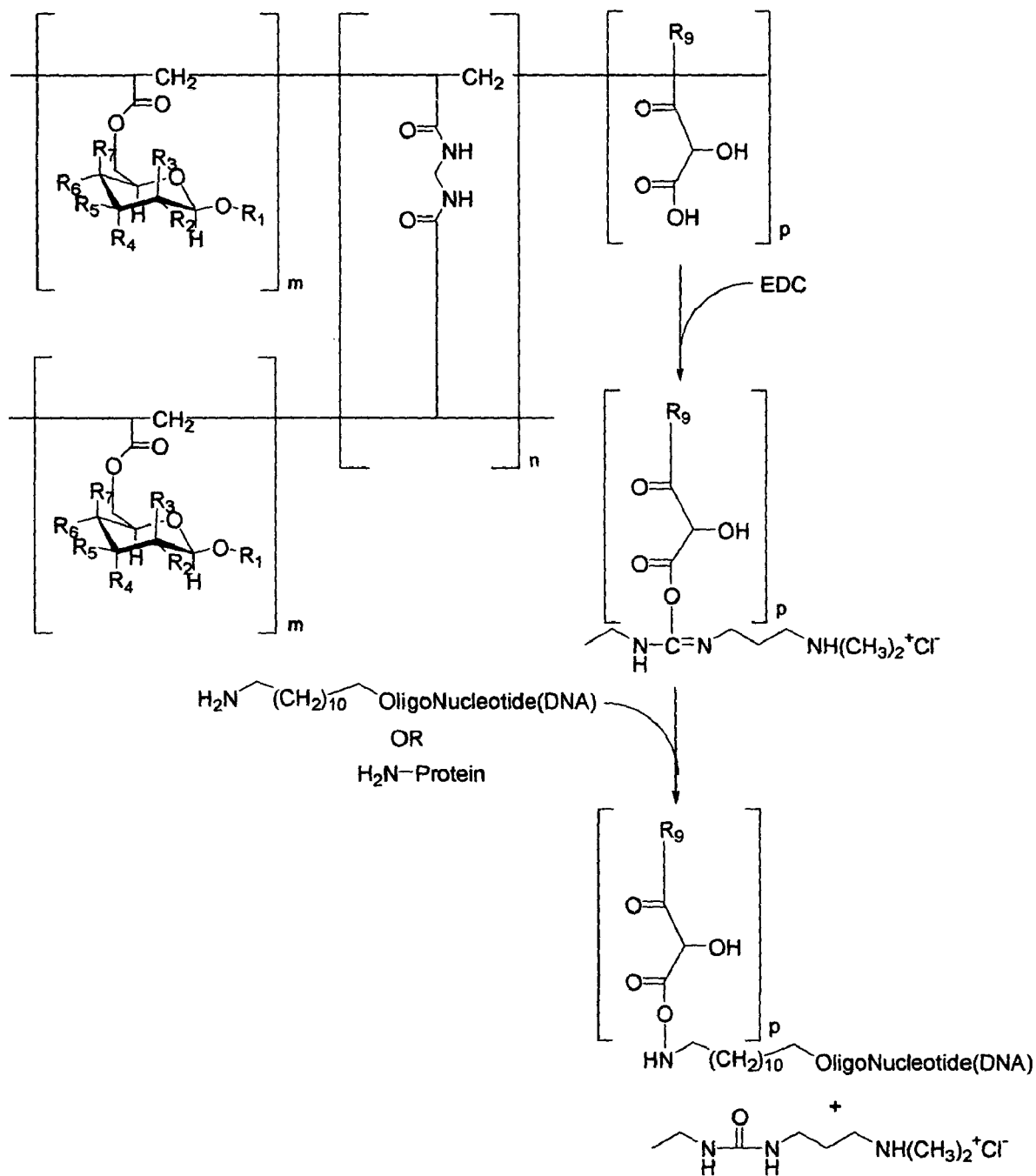

FIG. 4. is a reaction diagram showing an EDC-mediated activation of a carboxylate moiety in the gel polymer network, and further reaction of the activated moiety with an amino group of an oligonucleotide, peptide, protein, or other biomolecule resulting in covalent attachment of the latter.

Figure 5:
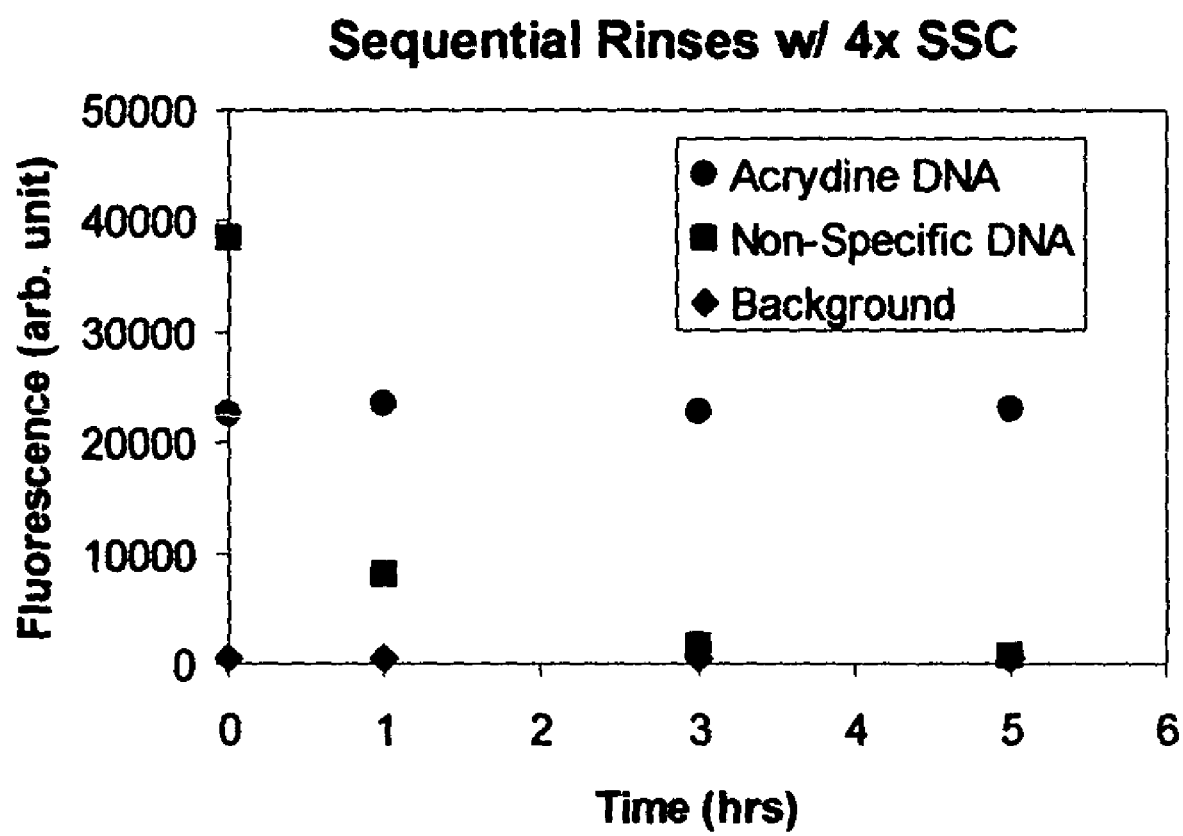

FIG. 5. demonstrates that there is very little non-specific bonding of target molecules to the sugar hydrogels of this invention.

Figure 6:
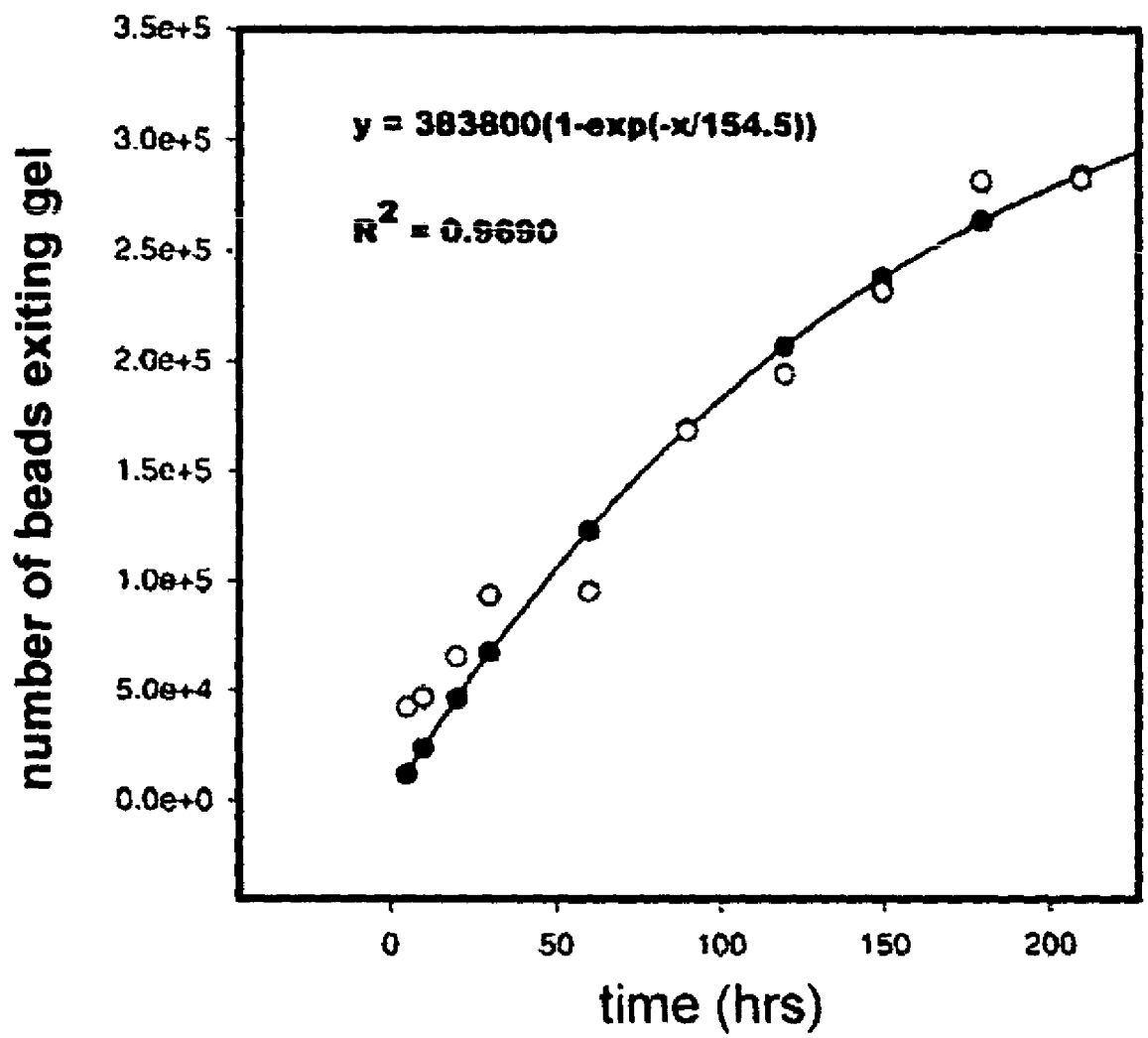

FIG. 6. describes the time-dependent movement of fluorescent 2-micron diameter beads through an unmodified sugar poly(acrylate) hydrogel. Open circles, experimental data; filled circles, diffusion theory.

Figure 7:
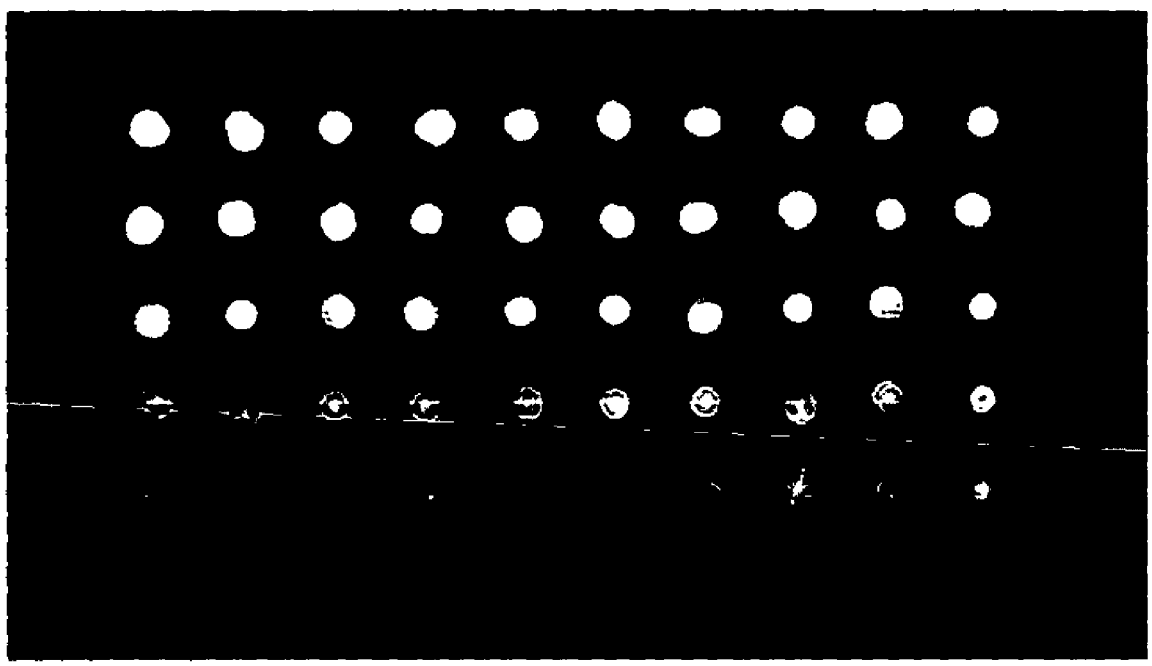

FIG. 7. shows a micro array formed using the reaction an amino terminated DNA labeled in the 5' end with a florophore (Cy3) with an activated amino sugar hydrogel of the invention on a support.

Figure 8:
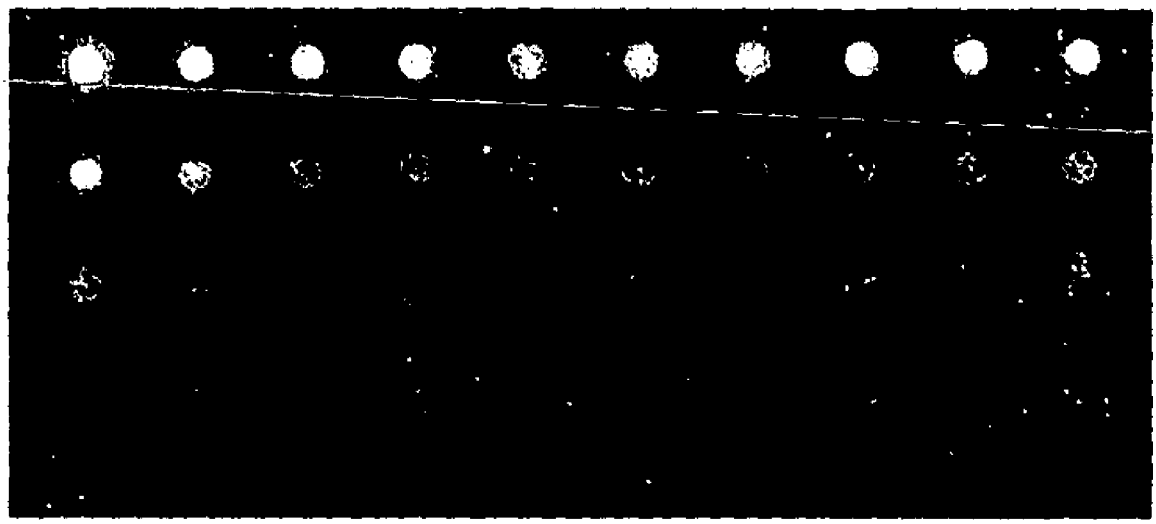

FIG. 8. shows a micro array of the DNA of FIG. 4 after reaction with a carboxylate-modified sugar hydrogel on a support.

Figure 9:
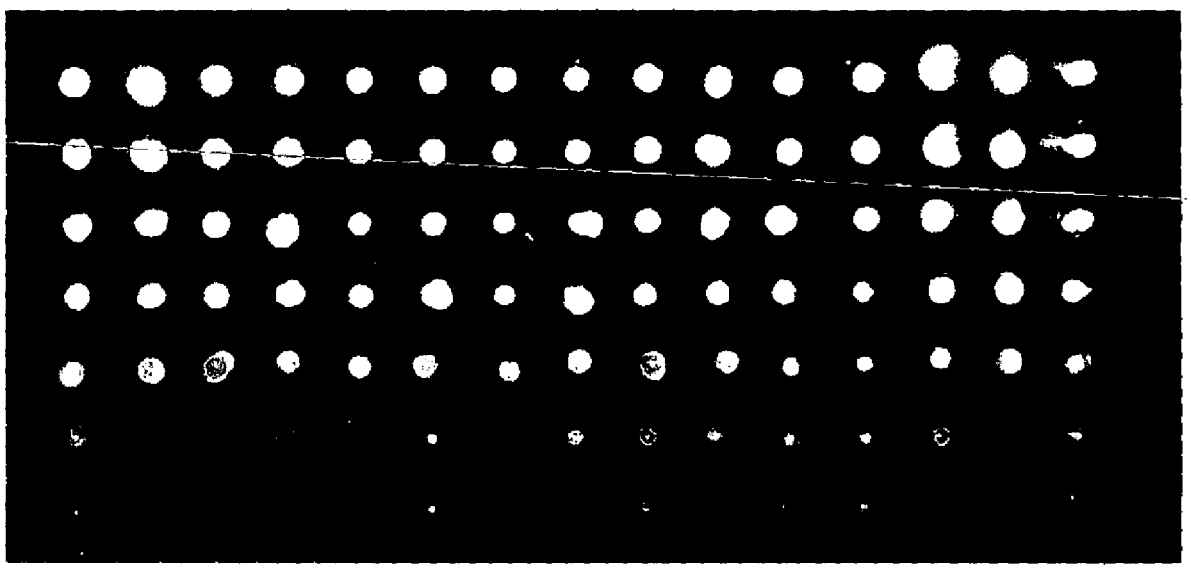

FIG. 9. shows a micro array of a fluorophore labeled protein coupled to a carboxylate modified sugar hydrogel on a support.

EXPERIMENTAL RESULTS

The galactose acrylate monomer, 6-acryloyl-β-O-methyl galactopyranoside (1) where $R_1$ is CH3 was chemoenymatically prepared using the procedure of Martin et al, 1992. The lipase from *Pseudomonas cepacia* catalyses the regioselective acryloylation at the 6-hydroxl moiety of β-O-methyl galactopyranoside in anhydrous pyridine to give the monoacrylate. The acrylate (1) exists as α and β anomers and either or both may be used to create the sugar hydrogels of this invention.

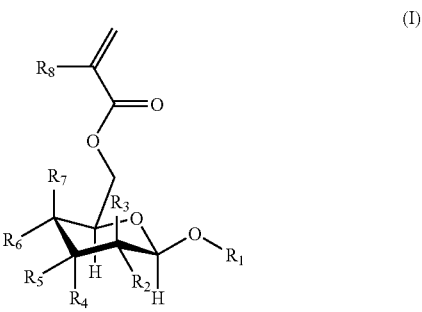

In structure (1) and all sugar acrylates or sugar methacrylates used in this invention, $R_1$ is preferably a methyl group, $R_2$-$R_7$ are preferably H or OH. For sugar acrylate, $R_8$ is H; for sugar methacrylate, $R_8$ is methyl. However, $R_1$ may also be without limitation, H, alkyl, aromatic, carbohydrate, and acryl and acrylamido. $R_2$-$R_7$ may be in addition to H, or OH, isopropyl, alkyl, aromatic. It should be understood that other groups may be selected for $R_1$, $R_2$, and $R_7$ without deviating from the bounds of this invention. The sugar compounds (1) of this invention may be mono, di, or polysaccharides.

Figure 1:
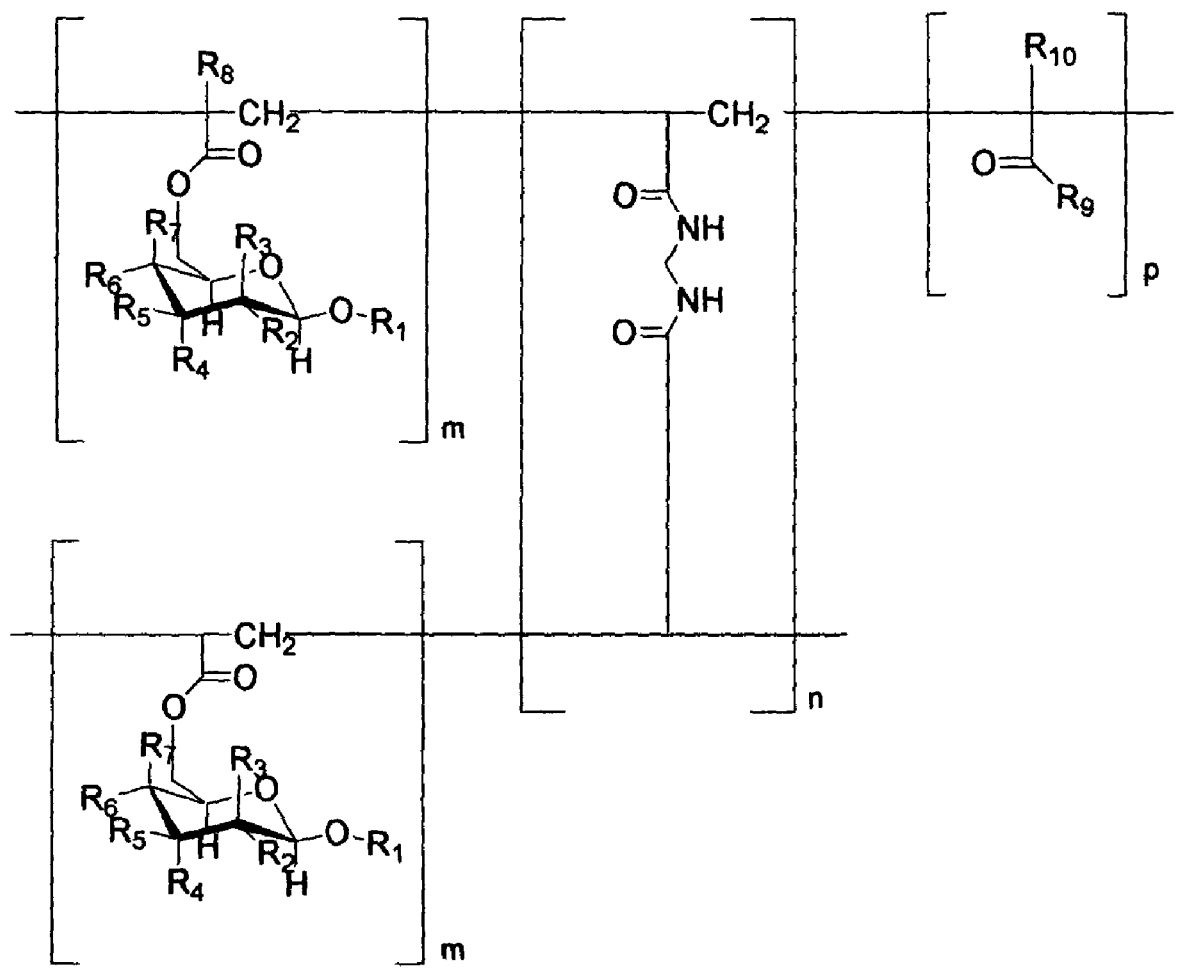
Figure 2:
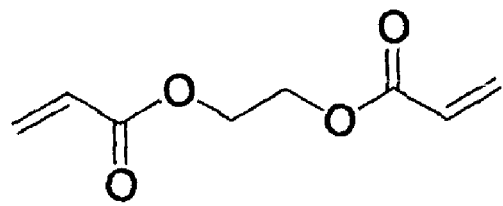
FIG. 2 shows the chemical structures of several carbon-carbon double-bond containing bis-crosslinkers that could be used to form the polymer network.
Figure 2:
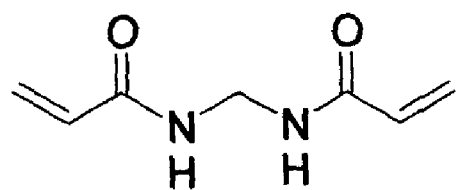
Figure 2:
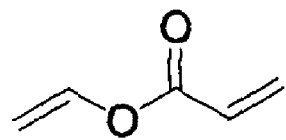
Figure 2:
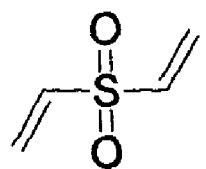

One possible generalized polymeric structure of the gel described in this invention is shown in FIG. 1. In this the sugar acrylate or methacrylate (1) of choice is polymerized with a multifunctional bis-crosslinker having at least two polymerizable double bonds and a third compound having a polymerizable double bond and an amine, carboxyl or other group capable of forming covalent bonds with oligonucleotides and/or proteins. The crosslinking compounds are selected from bis-acrylamides, bis-acrylates and bis-vinyl compounds (FIG. 2). The third compound is selected so that when the sugar hydrogel polymer is formed, the amino or carboxyl groups of the third compound provide reactive sites on the polymer backbone for reaction with coupling agents (FIG. 3) that allow covalent attachment of oligonucleotides and proteins and other biomolecules of interest. Covalent bonding of the polymer reactive sites with compounds of interest provides the basis of assay for the target molecules of interest.

Copolymerization of Acrydine DNA with Sugar Acrylate

Oligonucleotides containing an acrylic acid group directly attached to their 5'-end were purchased from Integrated DNA Technologies. Samples were prepared on glass slides that had been functionalized with methacrylate groups using the following procedure. The glass slide is cleaned a by immersion in a hydrochloric acid/methanol mixture, followed by sulfuric acid and treated with a 4% (v/v) solution of methacryloxypropyl trimethoxysilane (MTPTS) (93 mL methanol, 2.7 mL water, 0.3 mL glacial acetic acid, 4 mL of silane) at 60° C. for 1 hour. The slides are then rinsed in methanol, water, and methanol again. The slides are baked for 5 minutes at 120° C. Slides can be stored in a dessicator for a period of a few weeks with no loss of activity.

The galactose acrylate (1) was dissolved in deionized water at a concentration of 20-40% (w/v), along with the crosslinker N,N'-Methylene-bis-acrylamide at 3-4% (w/w) of the monomer concentration and the acrydine DNA at a concentration of 0.1-1 mole % of the bis-acrylamide concentration. This procedure uses a few nmoles of DNA for a 1 mL synthesis. The polymerization is accomplished via a free radical polymerization, common for formation of poly(acrylamide) gel matrixes. N,N,N',N'-tetramethyl ethylenediamine (TEMED) and sodium persulfate are used to initiate polymerization. This scheme is depicted below.

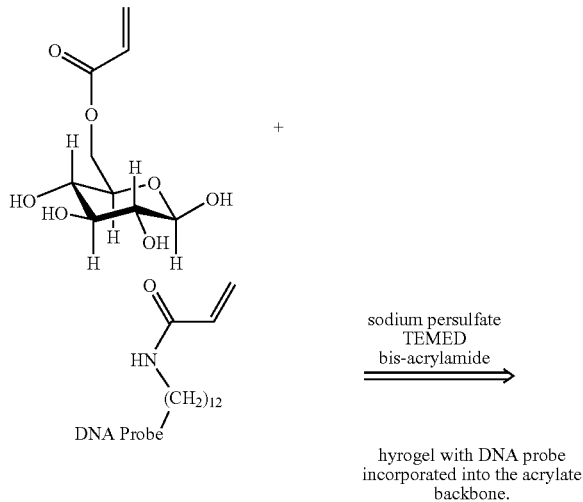

We have applied this technique to oligonucleotides containing 20 bases with an acrylate group on the 5' end and a fluorophore (Cy3) on the 3' end. FIG. 2. shows the fluorescence intensity of the immobilized DNA (circles). The intensity does not change with repeated washings indicating the DNA is covalently immobilized. On the other hand, when non-acrylated DNA is used (squares), the fluorescent intensity decreases to the background level (diamonds) after two washes. This shows that there is extremely low non-specific absorption of target molecules to the sugar acrylate gel. This provides the low background levels necessary for ultrasensitive detection.

Formation of Amino-Modified Sugar Acrylate Hydrogel

Thin hydrogels (~100 micron thickness) were formed on glass slides that had been functionalized with acrylic groups through the procedure above. The galactose acrylate (1) was dissolved in deionized water at a concentration of 20-40% (w/v), along with N, N methylene bis-acrylamide cross-linker at 3-4% (w/w) of the monomer concentration and N-(3-aminopropyl) methacrylamide 4-5% (w/w) of the sugar acrylate monomer concentration. The polymerization is accomplished via a free radical polymerization using the initiators TEMED and sodium persulfate.

Figure 3:
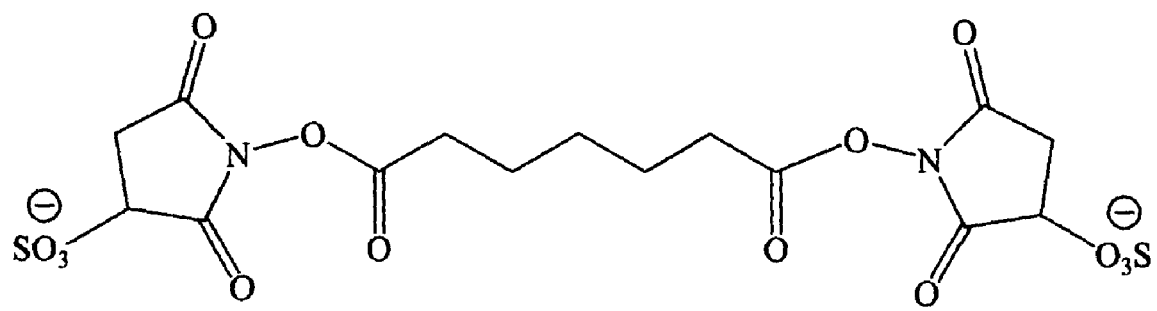
FIG. 3 shows the structure of two crosslinkers used to attach DNA, peptides, proteins, or other biomolecules via amine linkages—$BS^3$ (top) and EDC (bottom).
Figure 3:
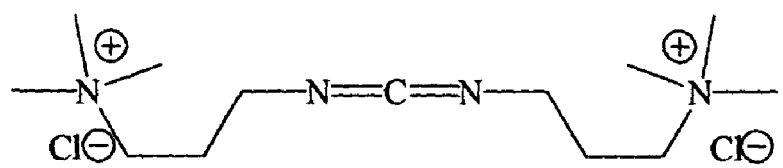

In order to study the porosity of the sugar acrylate gel, we measured the passive diffusion of fluorescently labeled beads through a non-modified sugar acrylate hydrogel. FIG. 3. shows the diffusion of FITC-labeled 2 micron diameter polystyrene beads through poly(6-acryloyl-β-O-methyl galactopyranoside) hydrogel swollen in 0.25 M PBS. The gel had a 94 wt % aqueous solution content. The curve fit indicates that at t=∞, ~384,000 beads will have passed through the gel into the receiving chamber. When the experiment was done with no gel in place, at equilibrium ~2,110,000 beads had entered the receiving chamber. Thus, 3.84/21.1 or ~18% of the beads that enter the gel actually pass completely through it, and the remaining 82% become trapped, indicating that the large pores are interconnected, and allow significant diffusion of the 2 micron spheres through the gel volume. The gels can be formulated to have a pore size ranging from 0.1 microns in diameter to 0.6 microns in diameter using the original synthesis conditions described previously (Martin, 1998), and by using the synthesis conditions described herein, pore sizes of significantly greater than 2 microns in diameter can clearly be achieved.

Linking of Oligonucleotides to Amino Sugar Gel

The amino moieties that have been linked into the gel are activated for attachment to an aminated oligonucleotides segment using a water soluble homobifunctional crosslinker bis (sulfosuccinimidyl) suberate ($BS^3$) which contains a reactive n-hydroxysuccinimide ester (NHS-ester). The crosslinker is added to the gel under acidic conditions (10 mM sodium phosphate, pH 6.0) at a concentration of 2.5 mM $BS^3$ and allowed to react for 1 hour to form a stable covalent amide bond. This creates an amine reactive group on the backbone of the gel. The entire scheme is depicted below.

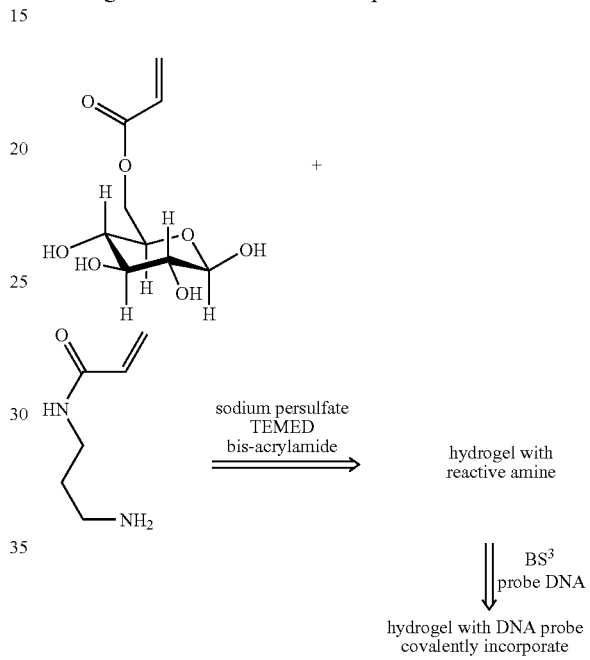

The amino terminated DNA is then added spot-wise to the activated gel using a BioChip non-contact microdispensing system. The microarrayer prints an array of oligonucleotides (900 pL per spot) resulting in a spot diameter of 300 μm and an interelement distance of 500 μm. The concentration of oligonucleotide was from 6.25 μM to 100 μM. The DNA is allowed to react with the activated substrate for 12 hours. The gel is then rinsed three times with a 4× saline sodium citrate buffer solution (0.60 M NaCl, 60 mM sodium citrate) to remove unattached DNA segments. We have applied this technique to oligonucleotides containing 24 bases with an amino group on the 3' end and a fluorophore (Cy3) on the 5' end. The resulting array can then be visualized using a conventional fluorescent array reader. FIG. 4 below shows a photograph of a 10×5 array created in this manner, where the rows are a serial dilution of the DNA. Each row contains a replicate of ten spots, with a dilution by 2 between rows (top row=100 μM, second row=50 μM, third row=25 μM, fourth row=12.5 μM, bottom row=6.25 μM). Note that these arrays appear approximately one-hundred times brighter relative to the same concentration spotted onto a flat, aminosilane substrate using the same crosslinking procedure.

Formation of Carboxylate-Modified Sugar Acrylate Hydrogel

Thin hydrogels (~100 micron thickness) were formed on glass slides that had been functionalized with acrylate groups through the procedure above. The galactose acrylate (1) was dissolved in deionized water at a concentration of 20-40% (w/v), along with the cross-linker N,N'-Methylene-bis-acrylamide at 3-4% (w/w) of the monomer concentration and 2-acrylamidohydroxyacetic acid 4-5% (w/w) of the sugar acrylate monomer concentration. The polymerization procedure is the same as for the amino-modified hydrogel.

Linking of Oligonucleotides to Carboxy Sugar Gel

Five µmoles of 1-ethyl-3-(3-dimethylaminopropyl) carbodiimide-HCL (EDC) are added to the amino terminated oligonucleotide solution at pH 7.2-7.4. The DNA/EDC solution is then added spot-wise to the gel using a non-contact microdispensing system. The DNA is allowed to react with the gel matrix for 12 hours at room temperature. The gel is then rinsed three times with 4× saline sodium citrate buffer solution to remove unattached DNA segments. We have applied this technique to the same amino modified oligonucleotides described above. We arrayed these oligos on a carboxylate-modified gel in a serial dilution starting at 25 µM. FIG. 5 indicates that immobilization of the DNA is occurring, but the fluorescent intensity is lower than observed using the $BS^3$ crosslinker. Note that in this case we are starting at ¼ the density, so the top row here should be compared to the third row above.

Linking of Proteins to Amino Sugar Gel

An amino functionalized sugar acrylate was activated with $BS^3$ using the procedure described above. The protein, Staphylococcal enterotoxin B (SEB), prepared in 10 mM sodium phosphate, pH 7.4 reacts with the NHS-ester gel support. Reaction of the ester with the lysine moiety of the protein provides the final amide linkage to the gel substrate.

Linking of Proteins to Carboxy Sugar Gel

A carboxy-functionalized sugar acrylate was activated using carbodiimide chemistry as described above. The protein, Cy3-labeled Staphylococcal enterotoxin B (SEB), prepared in 10 mM sodium phosphate, pH 7.4 was allowed to react with the carboxylic acid moiety in the presence of EDC. Reaction of the carboxylic acid group with the primary amines of the protein provided a stable covalent amide linkage between the protein and the gel substrate. The SEB solution (concentration range 0.1 µg/mL to 200 µg/mL) was deposited in replicates of 15 onto the modified gel using the BioChip microarrayer. Each printed element had 300 µm spot diameter, 900 pL print volume, and 500 µm inter-element distance. The protein modified gel slides were rinsed briefly with PBS, pH 7.4, $H_2O$, air dried and subsequently stored at 4° C. FIG. 6. shown below indicates that we are getting significant immobilization of the Cy5-labeled SEB with the carboxylated sugar acrylate gel.

Methods for assaying biomolecules of interest include well known optical, fluorescence, and radioactivity means and the like, depending on specific molecules selected for assay.

The invention claimed is:

1. A method for assaying biomolecules wherein said assay is selected from the group consisting of a fluorescence assay, a radioactive assay, a magnetic assay and an optical assay, comprising the steps of:
    (A) functionalizing a support with acrylate groups;
    (B) forming a polyacrylate hydrogel by reacting a 6-acryloyl-beta-O-methyl monosaccharide with a crosslinker with two or more polymerizable double bonds, and 2-acrylamido hyrdroxyacetic acid,
    (C) reacting said polyacrylate hydrogel with said acrylate groups of said support to form a polyacrylate hydrogel linked to a support,
    (D) reacting said biomolecule to be assayed with a second crosslinker and said polyacrylate hydrogel thereby forming a covalent bond between said biomolecule and said second crosslinker and a covalent bond between said second crosslinker and said polyacrylate hydrogel linked to said support, and
    (E) assaying said covalently bonded biomolecule.

2. The method of claim 1, wherein said biomolecule is a DNA.

3. The method of claim 2, wherein said DNA comprises up to 100,000 nucleotide base units.

4. The method according to claim 1, wherein said polyacrylate hydrogel is a network and said polyacrylate hydrogel has a pore size of 0.1-10µ.

5. The method according to claim 4, wherein the polyacrylate is a three-dimensional, macroporous substrate used for the immobilization of oligonucleotides, peptides and proteins.

6. The method according to claim 1, wherein said biomolecule is CY3-Staphylococcal enterotoxin B (SEB).

7. The method according to claim 1 wherein said biomolecule is a protein.

8. The method according to claim 1 wherein said biomolecule comprises a fluorophore group.

* * * * *